United States Patent [19]

Cazers et al.

[11] Patent Number: 5,134,137

[45] Date of Patent: Jul. 28, 1992

[54] CEPHALOSPORIN ANTIBIOTICS

[75] Inventors: Alexander R. Cazers, Richland; K. Thomas Koshy; Prem S. Jaglan, both of Kalamazoo; Robert J. Yancey, Jr., Richland; Terry J. Gilbertson; Thomas S. Arnold, both of Kalamazoo; David B. Johnson; Catherine L. Gatchell, both of Portage, all of Mich.

[73] Assignee: The Upjohn Company, Kalamazoo, Mich.

[21] Appl. No.: 460,346

[22] PCT Filed: Oct. 11, 1988

[86] PCT No.: PCT/US88/03435

§ 371 Date: May 9, 1990

§ 102(e) Date: May 9, 1990

[87] PCT Pub. No.: WO89/04313

PCT Pub. Date: May 18, 1989

Related U.S. Application Data

[63] Continuation of Ser. No. 118,974, Nov. 10, 1987, abandoned, which is a continuation of Ser. No. 142,760, Jan. 11, 1988, abandoned, which is a continuation of Ser. No. 142,761, Jan. 11, 1988, abandoned, which is a continuation of Ser. No. 143,500, Jan. 11, 1988, abandoned.

[51] Int. Cl.$^5$ ................ C07D 501/36; A61K 31/545
[52] U.S. Cl. ................ 514/206; 540/226; 540/227
[58] Field of Search ............. 540/226, 221, 227; 514/202, 206

[56] References Cited

U.S. PATENT DOCUMENTS

| | | | |
|---|---|---|---|
| 4,278,671 | 7/1981 | Ochiai | 424/246 |
| 4,464,367 | 8/1984 | Labeeuw | 424/246 |
| 4,487,767 | 12/1984 | Takaya et al. | 540/227 |
| 4,510,138 | 4/1985 | Ochiai | 514/206 |
| 4,520,194 | 5/1985 | Ochiai | 544/22 |
| 4,950,661 | 8/1990 | Olliero et al. | 540/227 |

FOREIGN PATENT DOCUMENTS

| | | |
|---|---|---|
| 91799 D/50 | 4/1980 | Japan . |
| WO82/03395 | 10/1982 | PCT Int'l Appl. . |
| 85/7613 | 5/1986 | South Africa . |
| 0004313 | 5/1989 | World Int. Prop. O. . |

OTHER PUBLICATIONS

Derwent Abstract of J56139-494 Japanese published application Oct. 30, 1981 of Japanese application 042864 filed Apr. 3, 1980.

C. M. Macdonald et al., "Disposition of Cefotaxime in Rat, Dog and Man", Arzneimittel Forschung Drug Research, 34:1719-1723, (1984).

*Primary Examiner*—Nicholas S. Rizzo
*Attorney, Agent, or Firm*—Martha A. Gammill

[57] ABSTRACT

Cephalosporin compounds of Formulas II

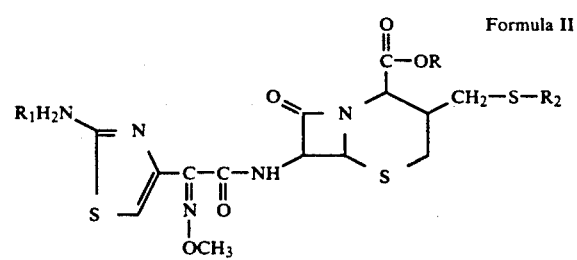

where

R is hydrogen or a pharmaceutical cation, in which case $R_1$ is not present, or R is hydrogen or a chemical bond when $R_1$ is an acid addition salt anion, and $R_2$ is (a) hydrogen, (b) a duplicate of the formula I compound to form a dimer, (c) an aminocarbonylmethyl, or (d) an —$SR_3$ group where $R_3$ is alkyl, cyclohexyl, phenyl, chloro-substituted phenyl, nitro-substituted phenyl, benzyl or furfuryl, have been found to be valuable as antibiotics for treating warm-blooded animals to combat pathogenic bacterial infections which cause diseases such as the commonly known "shipping fever".

6 Claims, No Drawings

CEPHALOSPORIN ANTIBIOTICS

CROSS-REFERENCE TO RELATED APPLICATIONS

This application is the national phase of co-pending international application PCT/US 88/03435, filed 11 Oct. 1988, which designated the U.S.; which is a continuation of U.S. application Ser. No. 118,974, filed 10 Nov. 1987; U.S. application Ser. No. 142,760, filed 11 Jan. 1988; U.S. application Ser. No. 142,761, filed 11 Jan. 1988; and U.S. application Ser. No. 143,500, filed 11 Jan. 1988, all of which are now abandoned.

INTRODUCTION

This invention relates to new cephalosporin antibiotics having a 7β-[2-(2-amino-1,3-thiazol-4-yl)-2-(Z)-(methoxyimino)acetamido]ceph-3-em-4-carboxylic acid or a pharmaceutically acceptable salt thereto, nucleus, and having part of its novelty focused on the 3-thiomethyl-ceph-3-em position thereof, which compounds are useful as antibiotics, primarily for treating valuable warm-blooded animals to resist, ward off or combat pathogenic infections caused by bacteria susceptible to these cephalosporin compounds.

BACKGROUND OF THE INVENTION

The cephalosporin antibiotic ceftiofur, named as 7-[2-(amino-1,3-thiazol-4-yl)-2-(methoxyimino)acetamido]-3-[(fur-2-ylcarbonyl)thiomethyl]-3-cephem-4-carboxylic acid, its alkali metal, alkaline earth metal and amine salts of the carboxylic acid group and easily hydrolyzable ester groups thereof are described and claimed in Labeeuw et al U.S. Pat. No. 4,464,367.

A hydrohalide salt of ceftiofur, particularly the hydrochloride salt thereof, was described and claimed in U.S. patent application Ser. No. 664,651 filed 25 Oct. 1984. A corresponding South African Patent No. 85/7613 has been published disclosing such ceftiofur hydrohalide salts.

Ochiai U.S. Pat. No. 4,278,671 and related U.S. Pat. Nos. 4,510,138 and 4,520,194 disclose some 7-[2-(2-aminothiazol-4-yl)-2-(syn)methoxyiminoacetamido]-cephalosporins. Many groups are described for positioning in the $R_3$ or 3-($R_3$—$CH_2$—) cephalosporin molecule position. Among the many such $R_3$ groups are mentioned hydroxy and mercapto at column 1, lines 67 and 68, but no specific compound such 3-mercaptomethyl type is named therein.

Desacetyl cefotaxime, 7-[2-(2-amino-1,3-thiazol-4-yl)-(syn)-2-methoxyiminoacetamido]-3-hydroxymethyl-ceph-3-em-4-carboxylic acid, is disclosed in a publication entitled "Disposition of Cefotaxime in Rat, Dog and Man" by C. M. Macdonald, et al in Arzneimittel Forschung Drug Research, 34 (II), No. 12 (1984), pp. 1719 to 1723, but such publication does not disclose the 3-mercaptomethyl compound of this invention or suggest the advantages which we have discovered according to this invention.

Published PCT application WO 82/03395 published Oct. 14, 1982 discloses some therapeutically active organic compounds which exhibit at least one group comprising the structure —S'S"—R, but it does not disclose the cephalosporin compounds claimed here.

Derwent Abstract No. 91799 D/50 of Japanese published application No. J56139-494 published Oct. 30, 1981 of Japanese application No. 042864 filed Apr. 3, 1980 discloses cephamycin disulfide symmetrical dimer compounds but it does not disclose the compounds claimed here.

OBJECTS OF THE INVENTION

It is an object of this invention to provide some new 7β-[-(2-amino-1,3-thiazol-4-yl)-2-(Z)-(methoxyimino)acetamido]ceph-3-em-4-carboxylic acid 3-position derivative antibiotic compounds as compounds per se.

It is another object of this invention to provide useful, veterinary pharmaceutical compositions containing as an active cephalosporin antibiotic component thereof one of the new 7β-[2-(2-amino-1,3-thiazol-4-yl)-2-(Z)-(methoxyimino)acetamido]ceph-3-em-4-carboxylic acid derivative, compounds of this invention, or a salt thereof.

It is another object of this invention to provide a method or process or use for treating a valuable warm-blooded animal to assist such animal to resist, ward-off or combat infections caused by bacteria susceptible to destruction, neutralization or elimination by administering to such animal an effective antibiotic amount of one of the new 7β-[-(2-amino-1,3-thiazol-4-yl)-2-(Z)-(methoxyimino)acetamido]ceph-3-em-4-carboxylic acid derivative compound of this invention or a pharmaceutically acceptable salt thereof.

SUMMARY OF THE INVENTION

Briefly, this invention provides some new cephalosporin antibiotic compounds, defined by formulas I or II on the STRUCTURE SHEET hereinafter, wherein R is hydrogen, or a selected pharmaceutically acceptable cation, in which latter case $R_1$ is not present, or R is hydrogen or a chemical bond when $R_1$ is a pharmaceutically acceptable acid addition salt anion, and $R_2$ is selected from the group consisting of
   (a) hydrogen,
   (b) a duplicate of the formula I or II compound molecule to the left of the $R_2$ position so that the total formula I or II compound is a dimer,
   (c) an aminocarbonylmethyl group, that is, a $H_2NC(O)CH_2$ moiety and
   (d) an —$SR_3$ group where $R_3$ is a
       $C_1$ to $C_6$-alkyl,
       cyclohexyl,
       phenyl,
       chloro-substituted phenyl,
       nitro-substituted phenyl,
       benzyl, or
       furfuryl.

In this description the formula I compounds are included within the definition scope of the formula II compounds.

This invention also includes pharmaceutical compositions comprising the new formula I or II compound, as described hereinabove, mixed with one or more pharmaceutically acceptable diluent components, as well as providing a new method, process or use for treating a valuable warm-blooded animal to resist, ward-off, combat or counteract infections by pathogenic bacteria susceptible to one of these new cephalosporin compounds of formula I or II by administering to said animal an antibacterially effective amount of a pharmaceutical composition containing one of the above new formula I or formula II compounds sufficient to protect the animal against or to combat bacterial infections.

PREFERRED EMBODIMENTS OF THE INVENTION

Preferred embodiments of this invention, illustrating the various possible 3-position substituents are set forth hereinbelow to further explain and exemplify the invention. The formula III to X compounds described hereinafter are included within formulas I and II described hereinabove.

FORMULA III AND IV COMPOUNDS

According to this aspect of the invention, we have discovered that 3-mercaptomethyl-7$\beta$-[2-(2-amino-1,3-thiazol-4-yl)-(Z)-2-(methoxyimino)acetamido]ceph-3-em-4-carboxylic acid (compound of formula III, which is within the definition of formula I), shown in its amino-acid form, but which can also exist in its inner salt or Zwitterionic form, is a useful antibiotic against a variety of veterinary clinically significant biological pathogen micro-organisms in its own right. We have discovered that it can be made as a stable compound which can be stored as a powder which is a stable compound form until it is ready for mixing into an appropriate pharmaceutical composition for administration to the valuable warm-blooded animal patient to assist the animal to resist, ward-off, combat or counteract the effects of infections by bacteria susceptible to this cephalosporin antibiotic compound. We have also discovered that this Formula I compound is biologically longer acting as an antibiotic than ceftiofur. In addition, and without wishing to being bound to any particular theory of action we believe that this Formula I or II compound sustained antibiotic action is due to its active 3-mercaptomethyl group, which the above prior art compound do not have. This 3-mercapto group of this compound can react rapidly with endogenous thiols and $R_2$-S-S-disulfide compounds from proteins and blood component compounds where $R_2$ denotes the residue of the animal blood or body proteins present in the body of the animal, which characteristic allows this antibiotic compound to be carried through or maintained in the animal body in the blood for a longer time than ceftiofur and be readily cleaved releasing the original active compound permitting the active compound to continue to perform its antibiotic function over a longer time period, so that the antibiotic need be administered to the animal less often than with other antibiotics.

The Formula III compound of in this invention can be used as such (Zwitterion form) or converted to a pharmaceutically acceptable salt (Formula IV) such as the alkali metal, alkaline earth metal or amine salt or heavier metal salt forms or an easily hydrolyzable ester thereof (Formula IV, R is hydrogen or the selected salt, e.g., the sodium, potassium, calcium, magnesium, zinc, cobalt, copper, dimethylamine, triethanolamine salts, and the like, or to a pharmaceutically acceptable acid addition salt thereof (Formula IV, $R_1$ is the selected addition acid group) such as the hydrochloride, hydrobromide, sulfate salts, or to an organic acid salt with acids such as methanesulfonic, p-toluenesulfonic, tert-butylsulfonic acid, and the like and R is hydrogen. The hydrochloric acid salt is presently preferred.

The Formula III compound can be chemically synthesized by a variety of methods from ceftiofur which is described and claimed in said above Labeeuw et al U.S. Pat. No. 4,464,367.

We have made our Formula III compound from ceftiofur as a dry, stable powder end product by three methods for hydrolyzing off the furoylcarbonyl moiety of ceftiofur, to leave as product of the process the desired Formula III compound a stable powder separated from the bulk of byproduct furoyl (furancarbonyl) derivatives such as furoyl carboxylic acid, furoyl chloride and alkali or acid salt byproducts, depending upon the form of the ceftiofur starting material. These methods are exemplified by detailed Examples 1 to 3 hereinbelow. Presently the method of Example 2, that involving the use of dithioerythritol, is preferred.

The compound of Formula III or Formula IV derivative thereof is useful as an active antibiotic drug compound in pharmaceutical dosage forms for treating valuable warm-blooded animals or humans. Presently, it is contemplated that this compound will be especially useful as a veterinary antibiotic drug to treat valuable warm-blooded animals such as cattle, horses, sheep, monkeys, goats, dogs, cats and the like to fight the effects of bacterial infections caused by organisms such as *Pasteurella hemolytica, P. multocida, Haemophilus pleuropneumonoiae, H. somnus, Escherichia coli,* Salmonella spp., *Staphylococcus aureus, Streptococcus agalactiae, Strep. bovis, Strep. dysgalactiae, Strep. faecatis, Strep. uberis, Salmonella typhimurium, E. coli, Staphyloccus aureus,* and the like, some of which are commonly associated with infections referred to as "shipping fever" in animals.

FORMULA V AND VI COMPOUNDS

According to another aspect of the invention, we have discovered that 1,1-bis[(7$\beta$)-(2-(2-amino-1,3-thiazol-4-yl)-(Z)-2-(methoxyimino)acetamido]ceph-4-carboxy-3-cephem-3-yl]dimethyldisulfide (compound of Formula V on the attached STRUCTURE sheets) shown in its amino-acid form, but which can also exist in its inner salt or Zwitterionic form, is a useful antibiotic against a variety of veterinary clinically significant biological pathogenic micro-organisms in its own right. We have discovered that it can be made as a stable compound which can be stored as a powder which is a stable compound form until it is ready for mixing into an appropriate pharmaceutical composition for administration to the valuable warm-blooded animal patient to assist the animal to resist, ward-off, combat or counteract the effects of infections by bacteria susceptible to this cephalosporin antibiotic compound. In addition, and without wishing to being bound to any particular theory of action, we believe that this Formula V or VI compound sustained antibiotic action is due to its active disulfide group. The disulfide group of this compound can split and react rapidly with endogenous thiols and $H_2$-S-S-disulfide compounds from proteins and blood component compounds where $R_2$ denotes the residue of the animal blood or body proteins present in the body of the animal, which characteristic allow this antibiotic compound to be carried through or maintained in the animal body in the blood and be readily cleaved releasing the original active compound permitting the active compound to continue to perform its antibiotic function over a longer time period, so that the antibiotic need be administered to the animal less often than with other antibiotics.

The Formula V compound of in this invention can be used as such (Zwitterion form) or converted to a pharmaceutically acceptable salt (Formula VI) such as the alkali metal, alkaline earth metal or amine salt or heavier metal salt forms (Formula VI, R is hydrogen or the selected salt, e.g., as the sodium, potassium, calcium, magnesium, zinc, cobalt, copper, dimethylamine, triethanolamine salts, and the like), or to a pharmaceutically acceptable acid addition salt thereof (Formula VI, $R_1$ is the selected addition acid group) such as the hydrochloride, hydrobromide sulfate salts, or to an organic acid salt with acids such as methanesulfonic, p-toluenesulfonic, tert-butylsulfonic acid, and the like and R is hydrogen. The hydrochloric acid salt is presently preferred.

The Formula V compound can also be named 3,3'[dithiobis(methylene)]bis[7-[[(2-amino-1,3-thiazol-4-yl)(methoxyimino))acetyl]amino]-8-oxo-[6R-[3[6'R,7'S-(2)]-6α,7β-(Z)]]5-thia-1-azabicyclo[4.2.0]-oct-2-ene-2-carboxylic acid, by the Chemical Abstracts system.

The Formula V compound can be chemically synthesized by a variety of methods from ceftiofur which is described and claimed in said above Labeeuw et al U.S. Pat. No. 4,464,367.

We have made our Formula V compound from ceftiofur as a dry, stable powder end product by three methods for hydrolyzing off the furoylcarbonyl moiety of ceftiofur and oxidizing the mercapto group to dimerize the 3-(mercapto-methyl)ceftiofur derivative, to leave as product of the process the desired Formula V compound a stable powder separated from the bulk of byproduct furoyl (furancarbonyl) derivatives such as furoyl carboxylic acid, furyl chloride and alkali or acid salt byproducts, depending upon the form of the ceftiofur starting material. These methods are exemplified by detailed Example 1 hereinebelow.

The compound of Formula V or Formula VI derivative thereof is useful as an active antibiotic drug compound in pharmaceutical dosage forms for treating valuable warm-blooded animals or humans. Presently, it is contemplated that this compound will be especially useful as a veterinary antibiotic drug to treat valuable warm-blooded animals such as cattle, horses, sheep, monkeys, goats, dogs, cats and the like to fight the effects of bacterial infections caused by organisms such as *Pasteurella hemolytica, P. multicida, Haemophilus pleuropneumoniae, H. somnus, Escherichia coli*, Salmonella spp., *Staphylococcus aureus, Streptococcus agalactiae, Strep. bovis, Strep. dysgalactiae, Strep. faecatis, Strep. uberis, Salmonella typhimurium, E. coli, Staphyloccus aureus*, and the like, some of which are commonly associated with infections referred to as "shipping fever" in animals.

According to another aspect of the invention, we have discovered that 3(aminocarbonylmethylthiomethyl)-7β-[2-(2-amino-1,3-thiazol-4-yl)-(Z)-2-(methoxyimino)acetamido]ceph-3-em-4-carboxylic acid (compound of Formula VII on the attached STRUCTURE sheets) shown in its amino-acid form, but which can also exist in its inner salt or Zwitterionic form, is a useful antibiotic against a variety of veterinary clinically significant biological pathogen microorganisms in its own right. We have discovered that it can be made as a stable compound which can be stored as a powder which is a stable compound form until it is ready for mixing into an appropriate pharmaceutical composition for administration to the valuable warm-blooded animal patient to assist the animal to resist, ward-off combat or counteract the effects of infections by bacteria susceptible to this cephalosporin antibiotic compound. In addition, and without wishing to being bound to any particular theory of action we believe that this Formula VII or VIII compound sustained antibiotic action is due to its active 3-(aminocarbonylmethylthiomethyl) group. This 3-(aminocarbonylmethylthiomethyl) group of this compound can react rapidly with endogenous thiols and $R_2$-S-S-disulfide compounds from proteins and blood component compounds where $R_2$ denotes the residue of the animal blood or body proteins present in the body of the animal, which characteristic allows this antibiotic compound to be carried through or maintained in the animal body in the blood and be readily cleaved releasing the original active compound permitting the above compound to continue to perform its antibiotic function over a longer time period, so that the antibiotic need be administered to the animal less often than with other antibiotics.

The Formula VII of compound in this invention can be used as such (Zwitterion form) or converted to a pharmaceutically acceptable salt (Formula VIII) such as the alkali metal, alkaline earth metal or amine salt or heavier metal salt forms (Formula VIII, R is hydrogen or the selected salt cation). The sodium, potassium, calcium, magnesium, zinc, cobalt, copper, dimethylamine, triethanolamine salts, and the like, or to a pharmaceutically acceptable acid addition salt thereof (Formula VIII, $R_1$ is the selected addition acid group) such as the hydrochloride, hydrobromide sulfate salts, or to an organic acid salt with acids such as methanesulfonic, p-toluenesulfonic, tert-butylsulfonic acid, and the like and R is hydrogen can be made or used. The hydrochloric acid salt is presently preferred.

The Formula VII compound can be chemically synthesized by a variety of methods from ceftiofur, or alkali metal salts thereof, which are described and claimed in said above Labeeuw et al U.S. Pat. No. 4,464,367.

We have made our Formula VII compound from ceftiofur as a dry, stable powder end product, by hydrolyzing off the furoylcarbonyl moiety of ceftiofur, and then etherifying the ceftiofur residue with a haloacetamide, e.g., iodoacetamide, to leave as product of the process the desired Formula VII compound which can be separated and purified to a stable powder separated from the bulk of byproduct furoyl (furancarbonyl) derivatives such as furoyl carboxylic acid, furoyl chloride and alkali or acid salt byproducts, depending upon the form of the ceftiofur starting material. This method is exemplified by detailed Example 1 hereinbelow.

The compound of Formula VII of Formula VIII derivative thereof is useful as an active antibiotic drug compound in pharmaceutical dosage forms for treating valuable warm-blooded animals or humans. Presently, it is contemplated that this compound will be especially useful as a veterinary antibiotic drug to treat valuable warm-blooded animals such as cattle, horses, sheep, monkeys, goats, dogs, cats, and the like to fight the effects of bacterial infections caused by organisms such as *Pasteurella hemolytica, P. multicida, Haemophilus pleuropneumonoiae, H. somnus, Escherichia coli*, Salmonella spp., *Staphylococcus aureus, Streptococcus agalactiae, Strep. bovis, Strep. dysgalactiae, Strep. faecatis, Strep. uberis, Salmonella typhimurium, E. coli, Staphyloccus aureus*, and the like, some of which are commonly associated with infections referred to as "shipping fever" in animals.

FORMULA IX AND X COMPOUNDS

According to another aspect of the invention, we have discovered that new 3-($C_1$ to $C_6$-alkyl-, cyclohexyl-, benzyl-, phenyl-, chlorophenyl- nitrophenyl- and furfuryl-dithiomethyl)-7β-[2-(2-amino-1,3-thiazol-4-yl)-(Z)-2-(methoxyimino)acetamido]ceph-3-em-4-carboxylic acids (compounds of Formula IX on the attached STRUCTURE sheets) shown in its amino-acid form, but which can also exist in its inner salt or Zwitterionic form, are useful antibiotics against a variety of veterinary clinically significant biological pathogen microorganisms in their own right. We have discovered that these compounds can be made as stable compounds which can be stored as a powder which are a stable compound form until such compound is ready for mixing into an appropriate pharmaceutical composition for administration to the valuable warm-blooded animal patient to assist the animal to resist, ward-off, combat or counteract the effects of infections by bacteria susceptible to one of these cephalosporin antibiotic compounds. In addition, and without wishing to being bound to any particular theory of action we believe that this Formula IX or X compound sustained antibiotic action is due to its active 3-($C_1$ to $C_6$-alkyl-, cyclohexyl-, benzyl-, phenyl-, chlorophenyl-, nitrophenyl- or furfuryl-dithiomethyl) group, which the above prior art compound do not have. These 3-(R-SS-methyl) groups of these compounds can react rapidly with endogenous thiols and $HR_2$-S-S-disulfide compounds from proteins and blood component compounds where $R_2$ denotes the residue of the animal blood or body proteins present in the body of the animal, which characteristic allows these antibiotic compounds to be carried through or maintained in the animal body in the blood and be readily cleaved when necessary to permit the compound to perform its antibiotic function over a longer time period, so that the antibiotic need be administered to the animal less often than with other antibiotics.

The Formula IX compound of in this invention can be used as such (Zwitterion form) or converted to a pharmaceutically acceptable salt (Formula X) such as the alkali metal, alkaline earth metal or amine salt or heavier metal salt forms (Formula X, R is hydrogen or the selected salt cation). The sodium, potassium, calcium, magnesium, zinc, cobalt, copper, dimethylamine, triethanolamine salts, and the like, or to a pharmaceutically acceptable acid addition salt thereof (Formula X, $R_1$ is the selected addition acid group) such as the hydrochloride, hydrobromide sulfate salts, or to an organic acid salt with acids such as methanesulfonic, p-toluenesulfonic, tert-butylsulfonic acid, and the like and R is hydrogen can be made and used. The hydrochloric acid salt is presently preferred.

The Formula IX compound can be chemically synthesized by a variety of methods from ceftiofur which is described and claimed in said above Labeeuw et al U.S. Pat. No. 4,464,367.

We have made our Formula IX compounds from a ceftiofur salt as a dry, stable powder end products, by hydrolyzing off the furoylcarbonyl moiety of ceftiofur, and esterifying the 3-mercapto group of the resulting intermediate to leave as product of the process the desired Formula IX compound which can be separated and purified to obtain the product as a stable powder separated from the bulk of byproduct furoyl (furancarbonyl) derivatives such as furoyl carboxylic acid, furoyl chloride and alkali or acid salt byproducts, depending upon the form of the ceftiofur starting material.

The compounds of Formula IX, or the Formula X derivative thereof, is useful as an active antibiotic drug compound in pharmaceutical dosage forms for treating valuable warm-blooded animals or humans. Presently, it is contemplated that this compound will be especially useful as a veterinary antibiotic drug to treat valuable warm-blooded animals such as cattle, horses, sheep, monkeys, goats, dogs, cats and the like to fight the effects of bacterial infections caused by organisms such as *Pasteurella hemolytica, P. multocida, Haemophilus pleuropneumonoiae, H. somnus, Escherichia coli,* Salmonella spp., *Staphylococcus aureus, Streptococcus agalactiae, Strep. bovis, Strep. dysgalactiae, Strep. faecatis, Strep. uberis, Salmonella typhimurium, E. coli, Staphyloccus aureus,* and the like, some of which are commonly associated with infections referred to as "shipping fever" in animals.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification. Examples of suitable dosage unit forms in accordance with this invention are tablets, capsules, orally administered liquid preparations in suitable liquid vehicles, sterile preparations in suitable liquid vehicles for intramuscular and intravenous administration, suppositories and sterile dry preparations for the extemporaneous preparation (mixing just prior to administration) of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of this antibiotic active ingredient in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, alginates, tragacanth, pectin, kelgin, carragenan, acacia, polyvinylpyrrolidone, polyvinyl alcohol, and the like, to increase the viscosity of the composition. In the case of injectable forms, the injectable formulation must be sterile and must be fluid to the extent that easy syringeability exists. Such preparations must be stable under the conditions of manufacture and storage, and ordinarily contain in addition to the principal solvent or suspending liquid, preservatives in the nature of bacteriostatic and fungistatic agents, for example, parabens, chlorobutanol, benzyl alcohol, benzoic acid, phenol, thimerosal, and the like to preserve the composition against microorganisms. In many cases, it is preferable to include osmotically active agents, for example, sugars or sodium chloride in isotonic concentrations. Carriers and vehicles include vegetable oils, dimethylacetamide, dimethylformamaide, ethyl lactate, ethyl carbonate, isopropyl myristate, ethanol, polyols, for example, glycerol, propylene glycol, liquid polyethylene glycol, and the like. Any solid preparations for subsequent extemporaneous preparation of sterile injectable preparations are sterilized, by exposure to steam, cobalt 60 irradiation, or by exposure to a sterilizing gas, for example, ethylene oxide. The aforesaid carriers, vehicles, diluents, surfactants, excipients, preservatives, isotonic agents and the like constitute the pharmaceutical means which adapt the preparations for systemic administration.

In these pharmaceutical compositions it may be desirable to include a viscosity increasing agent such as sodium carboxymethylcellulose (sodium CMC). Other suitable viscosity increasing agents can be substituted for sodium CMC.

The pharmaceutical dosage unit forms of the compounds of this invention are prepared in accordance with the preceding general description to provide from about 1 mg. to about 500 mg of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain antibiotic effects within the aforesaid effective non-toxic range. Expressed otherwise, when used systemically, an amount of the essential active ingredient (Formula I or II compound) is provided to a recipient within a range from about 0.2 mg./kg. to about 100 mg./kg. of body weight of the recipient.

Preferred dosages for most applications are 0.2 mg./kg. to 10.0 mg./kg. of body weight of the essential active ingredient antibiotic compound depending upon the animal being treated. In a topical semi-solid ointment formulation the concentration of the active ingredient may be 1%-20%, preferably 5%-10% in a carrier, such as a pharmaceutical cream base.

The useful pharmaceutical dosage unit forms of these compounds in pharmaceutical formulations are preferably adapted for systemic administration to obtain antibiotic effects comprising an effective, non-toxic amount of the Formula II salt.

Further, the invention relates to methods of obtaining antibiotic effects in mammals, for example, valuable warm-blooded animals such as dogs, cats, horses, and other commercially valuable animals, by administering systemically to the mammals the aforesaid pharmaceutical dosage units forms supplying an effective, non-toxic amount of one of the compounds of this invention for antibiotic effects.

The invention is further illustrated by the following detailed examples.

EXAMPLE 1

Preparation of 3-mercaptomethyl-7$\beta$-[-2-(2-amino-1,3-thiazol-4-yl)-(Z)-2-(2)-(methoxyimino)acetamido]-ceph-3-em-4-carboxylic acid by hydrolysis of 3-(2-furoylthiomethyl)-7$\beta$-[2-(2-amino-1,3-thiazol-4-yl)-(Z)-2-(methoxyimino)acetamido]ceph-3-em-4-carboxylic acid, sodium salt Fifty milliliters of saturated KCl solution containing 0.5 gm. of tetrasodium ethylene diaminetetracetic acid (EDTA) and 0.4 gm. of sodium bisulfite was degassed by sonication in a 125 ml. Erlenmeyer flask. The mixture was cooled to 0° C. in an ice bath. To this cooled mixture was added 1.0 gm. of the above sodium salt starting material which was dispersed by sonication. Again the flask was cooled to near 0° C. The contents were stirred with a magnetic stirring bar under a nitrogen ($N_2$) atmosphere. Then there was added dropwise 3 ml. of col (about 0° C.) degassed 22.5% KOH base solution containing 0.5% tetrasodium EDTA. The base treated mixture was allowed to stand for one hour under $N_2$. By this time, all the starting material was hydrolyzed as judged by high performance liquid chromatography (HPLC) analysis of the reaction mixture. The solution was again cooled to 0° C. The solution was neutralized with cold 20% $H_3PO_4$ in water solution to a pH of 2.5. A pH meter was used. A thick yellowish white precipitate was obtained in suspension. The suspension was cooled to coagulate the precipitate in the suspension. The suspension was centrifuged in 50 ml. tubes and the supernatant was discarded. The precipitate was washed twice with cold degassed 0.2% acetic acid and once with cold degassed water, centrifuging and discarding the supernatant between each operation. The resulting solid was suspended in about 30-40 ml. of cold degassed water and lyophilized. About 0.4 gm. of a light yellow powder was obtained. This powder material was purified on a 2 gm. $C_{18}$ silica column eluted with cold 0°-4° C. degassed water. The effluent collected in 2 ml. fractions were monitored by HPLC for purity. The fractions containing the least amount of impurities were combined and lyophilized. The above named 3-mercaptomethyl- product was a very white amorphous powder with HPLC purity in the 75%-85% range.

The structure of the named 3-mercaptomethyl product compound was confirmed by infrared (IR), proton nuclear magnetic resonance (NMR) and free atom bombardment (FAB) mass spectra data. The FAB mass spectrum shows the main ion at 467, representing the potassium salt of the titled 3-mercaptomethyl product compound. The IR spectrum supports the structure except for the uncertainty of the free 3-mercaptomethyl group. The proton NMR spectrum shifts for the product are also in good agreement for the named 3-mercapto-methyl product, but NMR spectra cannot confirm or deny the presence of the sulfhydryl (—SH) group. The presence of the sulfhydryl group was confirmed by preparing the 3-(methylthiomethyl)-derivative of the above-named end product by reacting the above-named 3-mercaptomethyl- compound with methyl iodide. The structure of the Formula I compound was confirmed by IR, NMR and mass spectra analysis. It can be obtained as a white powder. It is stable in the dry state. The mass spectra for this compound shows a very strong mass ion at 412. The chemical shifts on the proton NMR spectrum shows absence of furoic acid and the presence of shifts at 6.8, 5.94, 5.16 and 3.96 ppm. In alkaline solution the Formula I compound decomposes quickly. In strongly acidic media the Formula I compound is converted to the 3,4-thio-lactone derivative.

EXAMPLE 2

Preparation of 7β-[2-(2-amino-1,3-thiazol-4-yl)-(Z)-2-(methoxyimino)acetamido]-3-mercaptomethyl-ceph-3-em-4-carboxylic acid via a reductive cleavage of sodium 7β-[2-(2-amino-1,3-thiazol-4-yl)-(Z)-2-(methoxyimino)acetamido] -3-(2-furoylthiomethyl)-ceph-3-em-4-carboxylate salt A one gram portion of sodium of sodium ceftiofur, 7β-[2-(2-amino-1,3-thiazol-4-yl)-(Z)-2-(methoxyimino)acetamido]-3-(2-furoylthiomethyl)ceph-3-em-4-carboxylate sodium salt is dissolved in 20 ml. of water in a 50 ml. glass stoppered centrifuge tube, or one gram of the hydrochloride salt of ceftiofur, 7β-[2-(2-amino-1,3-thiazol-4-yl)-(Z)-2-(methoxyimino)acetamido]-3-(2-furoylthiomethyl)ceph-3-em-4-carboxylic acid, is suspended in 20 ml of water and small amounts of sodium bicarbonate powder are added until solution is achieved.

Separately, a 400 mg. portion of dithioerythritol is dissolved in 10 ml. of water. To the resulting solution 400 microliters of triethylamine is added and mixed with a glass rod.

The dithioerythritol solution is added to the ceftiofur solution. The resulting mixture becomes cloudy and then becomes thick. The reaction vessel is immersed in a water bath at 45°-50° C., and heated until the reaction mixture appears clear, about 15 to 20 minutes, when the reduction is complete.

The resulting reaction mixture is treated with 20% W/V orthophosphoric acid in water solution to adjust the pH of the mixture to 2.4 to 2.5 and then the mixture vessel is left in an acetone/dry ice bath at −10° C. for about 15 to 20 minutes. The resulting precipitate is isolated from the reaction mixture by centrifugation and washed free of furoic acid and inorganic salts with 0.2% W/V acetic acid in water solution and then lyophilized with water to obtain the 7β-[2-(2-amino-1,3-thiazol-4-yl)-)Z)-2-(methoxyimino)acetamido]-3-mercaptomethylceph-3-em-4-carboxylic acid in 54.4% yield with a 94% purity. The structure was confirmed by mass spectroscopy.

EXAMPLE 3

Preparation of 7β-[2-(2-amino-1,3-thiazol-4-yl)-(Z)-2-(methoxyimino)acetamido]-3-mercaptomethylceph-3-em-4-carboxylic acid by hydrolysis of a suspension of ceftiofur hydrochloride or sodium salt in methylene chloride A 1 gm. portion of ceftiofur hydrochloride or sodium salt is suspended in 90 ml. of methylene chloride in a 250 ml. Erlenmeyer flask. The salt lumps are broken down with a glass rod and the resulting powder is dispersed uniformly by sonication. To this resulting suspension there is added 33 ml. of a 1N potassium hydroxide in water solution containing 0.5% W/V ethylenediaminetetracetic acid (EDTA). The hydrolysis reaction to remove the furoyl group of ceftiofur so to form the corresponding 3-mercaptomethyl-compound is almost instantaneous. The potassium hydroxide aqueous liquid phase is separated from the organic liquid phase and diluted with 75 ml. of ice cold water. The diluted solution is acidified with cold 20% W/V orthophosphoric acid in water solution to a pH of 2.4 to 2.5 with stirring. The resulting suspension is left in an acetone/dry ice bath at −10° C. for about 15 to 20 minutes. The precipitate which forms is isolated by centrifugation and washed free of the furoic acid and inorganic byproducts with ice cold 0.2% W/V acetic acid aqueous solution and then lyophilized from water to obtain the 7β-[2-(2-amino-1,3-thiazol-4-yl)-(Z)-2-(methoxyimino)acetamido]-3-mercaptomethylceph-3-em-4-carboxylic acid product.

EXAMPLE 4  In Vitro

This example illustrates the effectiveness of the Formula III compound of this invention as an antibiotic against a variety of gram-negative veterinary pathogen microorganisms compared against ceftiofur and desacetylcefotoxime in terms of the minimum inhibitory concentration (MIC values), in standard laboratory tests conducted as follows:

Stock solution of each test antibiotic compound were prepared to have a concentration of 2 mg. of the test compound per milliliter in sterile water of 0.1M ammonium acetate solution. The amount of each compound used was adjusted for base compound activity as calculated from the purity data for the selected batch of compound.

The dilution procedure described by Washington and Sutter [*Manual of Clinical Microbiology*, 3rd, Edit. (Lennett, E. H. et al, Eds.), pp. 453-458 (1980), American Society for Microbiology, Washington, D.C.] was modified so that serial concentrations of 128 to 0.0625 microgram/ml. in sterile water was obtained. Then 1.5 ml. aliquots of these test antibiotic dilution mixtures are added to 13.5 molten (50° C.) Mueller-Hinton agar. Each resulting mixture is poured into 15×100 mm, sterile Petri plates and allowed to dry at room temperature overnight.

Test bacterial cultures are maintained at −70° C. on glass beads. [See R. J. Yancey, Jr. et al, *Amer. Jr. of Vet. Research*, 48, No. 7, pp. 1050-1053, (1987)]. At least one bacteria-laden bead per culture is dropped into one ml. of brain heart infusion (BHI) broth for overnight culture at 37° C. in 5% V/V carbon dioxide in air atmosphere.

On the data of assay, 2 to 8 drops of the bacterial broth cultures are transferred to fresh BHI broth (1 ml.) and the mixture is incubated for 4 to 6 hours at 37° C. in a 5% V/V carbon dioxide in air atmosphere. The resulting cultures are then diluted to match a 0.5 MacFarland standard and further diluted 1:20 V/V with sterile saline solution.

A 0.001 ml. drop of the resulting mixture, containing approximately $10^3$ to $10^4$ colony forming units (CFU) of each test bacteria organism, is dispensed onto the surface of the test antibiotic compound test plates with a Steer's type replicator. The resulting innoculated plates are incubated 16 to 18 hours at 37° C. with a carbon dioxide atmosphere. The minimal inhibitory concentration (MIC) is determined as the lowest concentration of test compound antibiotic that completely inhibited visable growth of the test bacterium.

IN VIVO

Experimental Infections and Antitiotic Treatment (for $ED_{50}$ in mice tests).

Systemic Infection Models

Mice are infected and treated with the test antibiotic compound according to procedures described previously [Yancey, Jr., R. J. et at. supra].

The test antibiotic compound is administered subcutaneously immediately following infection, then at 24 hours and 48 hours post infection. The medium effective dose ($ED_{50}$) number is determined for all infections. The $ED_{50}$ value is defined as the calculated concentration of the test antibiotic compound in mg. of compound per kilogram of mouse body weight per day at which 50% of the animals survived six days post infection.

By these in vitro procedures the MIC values of the Formula III compound compared to ceftiofur and desacetylcefotoxime were determined against the organisms listed in TABLES I and II.

The in vivo results ($ED_{50}$ values) for tests of the same three compounds in mice against two gram-negative pathogenic bacterial species are provided in TABLE III.

The MIC data in TABLES I and II illustrate that the Formula III compound of this invention is an effective antibiotic at comparative MIC concentrations against most of the organisms. The in vivo test data in TABLE III show similar $ED_{50}$ values for both the Formula III compound herein and ceftiofur. Results against the Salmonella typhimurium are illustrative of a longer serum half life for the Formula III compound due to its interaction via its mercapto (or sulfhydroyl) moiety with serum and tissue proteins.

Such a property in an antibiotic compound is desirable for use against infections by bacteria such as *Salmonella typhimurium* which are known to persist in tissues.

TABLE 1-continued
MIC VALUES FOR GRAM-NEGATIVE VETERINARY PATHOGENS

| ORGANISM | STRAIN | MIC 9µ/ML) | | |
|---|---|---|---|---|
| | | 1 | 2 | 3 |
| Pseudomonas aeruginosa | ATCC27853 | 32 | >32 | >32 |

*In vivo test strain
Compounds:
1 = ceftiofur
2 = Formula III compound
3 = desacetyl cefotoxime

TABLE II

| ORGANISM | STRAIN | MIC (µg/ml) | | |
|---|---|---|---|---|
| | | 1 | 2 | 3 |
| Staphylococcus aureus | UC6093 | 1.0 | 16 | 16 |
| | UC6097 | 0.5 | 16 | 16 |
| | UC9201 | 1.0 | 16 | 16 |
| | UC6688 | 32 | >32 | >32 |
| | ATCC25923 | 0.25 | 16 | 4.0 |
| Streptococcus agalactiae | UC3947 | ≦0.06 | ≦0.06 | ≦0.6 |
| | UC6892 | ≦0.06 | ≦0.06 | ≦0.06 |
| Strep. bovis | UC6281 | ≦0.06 | ≦0.06 | ≦0.06 |
| Strep. dysgalactiae | UC251 | ≦0.06 | ≦0.06 | ≦0.06 |
| Strep. faecalis | UC241 | >32 | >32 | >32 |
| | UC694 | >32 | >32 | >32 |
| | ATCC29212 | 32 | >32 | >32 |
| Strep. suis | 538-2 | ≦0.06 | ≦0.06 | ≦0.06 |
| | 650-2 | ≦0.06 | ≦0.06 | ≦0.06 |
| Strep. uberis | UC3946 | ≦0.06 | 0.25 | ≦0.06 |
| | UC6159 | 0.25 | 32.0 | 16 |
| Corynebacterium pyogenes | 213-2 | <0.06 | 0.25 | 0.25 |
| Micrococcus luteus | UC130 | 0.25 | 0.25 | ND |

Compounds:
1 = ceftiofur
2 = Formula III compound
3 = desacetyl cefotoxime
ND = not determined

TABLE III

| ORGANISM | STRAIN | $ED_{50}$ IN MG/KG (95% CONFIDENCE LIMITS) | | |
|---|---|---|---|---|
| | | 1 | 2 | 3 |
| P. hemolytica | UC6531 | 0.8 (0.6–1.1) | 0.8 (0.6–1.1) | 0.3 (0.2–0.4) |
| | UC6532* | 0.9 (0.6–1.3) | 0.8 (0.5–1.2) | 0.6 (0.4–0.9) |
| Sal. typhimurium | UC6162 | 0.4 (0.3–0.6) | 0.3 (0.2–0.5) | 0.8 (0.5–1.2) |
| | UC6164* | 0.5 (0.3–0.6) | 0.5 (0.4–0.8) | 1.0 (0.7–1.5) |

*β-lactamase producing strain (ampicillin $ED_{50}$ > 100 mg/kg)
† Compounds:
1 = Ceftiofur
2 = Formula III compound herein
3 = desacetylcefotoxime

TABLE 1
MIC VALUES FOR GRAM-NEGATIVE VETERINARY PATHOGENS

| ORGANISM | STRAIN | MIC 9µ/ML) | | |
|---|---|---|---|---|
| | | 1 | 2 | 3 |
| Pasteurella hemoyltica | UC6531* | ≦0.06 | ≦0.06 | ≦0.06 |
| | UC6532* | ≦0.06 | ≦0.06 | ≦0.06 |
| | B77-19 | ≦0.06 | ≦0.06 | ≦0.06 |
| P. multocida | B77-18 | ≦0.06 | ≦0.06 | ≦0.06 |
| Escherichia coli | UC3784 | 0.13 | 0.5 | 0.25 |
| | UC6720 | 0.13 | 0.5 | 0.25 |
| | P75-1 | 0.13 | 0.5 | 0.25 |
| | ATCC25922 | 0.13 | 0.5 | 0.25 |
| Salmonella choleraesuis | UC6073 | 1.0 | 2.0 | 0.5 |
| | UC6077 | 2.0 | 1.0 | 1.0 |
| Salmonella typhimurium | UC6162* | 0.25 | 0.5 | 0.13 |
| | UC6164* | 0.25 | 0.5 | 0.13 |
| Bordetella bronchiseptica | UC6313 | >32 | >32 | >32 |
| | UC3287 | >32 | >32 | >32 |

EXAMPLE 5

Preparation of 1,1-bis-(7β)-(2-(2-amino-1,3-thiazol-4-yl)-(Z)-2-(methoxyimino)acetamido-4-carboxy-3-cephem-3-yl)dimethyldisulfide by hydrolysis/oxidation of ceftiofur sodium salt A 0.5 gm. portion of ceftiofur sodium salt [sodium 7-[2-(2-amino-1,3-thiazol-4-yl)-2-(methoxyamino)acetamido]-3-[(fur-2-yl-carbonyl)thiomethyl]-3-cephem-4-carboxylate] was added to 25 ml. of ice cold (−2° C.) saturated potassium chloride solution containing 0.5% EDTA (ethylenediaminetetracetic acid) (degassed) and the mixture was dispersed by sonication procedure.

To this above dispersion/solution there was added dropwise with stirring 1.5 ml. of ice-cold degassed 22.5% potassium hydroxide solution containing 0.5% EDTA. The resulting mixture was allowed to stand in the cold atmosphere for 45 minutes, although this much time may not be necessary.

The resulting mixture was neutralized while stirring under nitrogen with cold degassed 20% ortho-phosphoric acid ($H_3PO_4$) to a pH of 6.

To this resulting neutralized mixture there was added 4 ml. of cold 10% hydrogen peroxide solution. The pH of the mixture was then 6. The mixture was allowed to stand in an ice bath for 0.5 hour. (Note: the solution formed a gel. It may be preferable to allow the solution to stand without placing it in an ice bath.)

The resulting reaction mixture container was removed from the ice bath and allowed to stand at room temperature for 0.75 hour. (Note: This may not be the optimum time. The mixture was allowed to stand this long because the HPLC analysis equipment was not available for checking the completion of the reaction on samples of the reaction mixture). After determinating the completion of the reaction, the mixture was still a gel so the reaction mixture was diluted with about 40 ml. of water at room temperature and the resulting mixture was transferred to a 125 ml. Erlenmeyer flask. The pH of the mixture was adjusted to pH 2.4 with cold 20% ortho-phosphoric acid solution. The resulting solution at this time was still quite thick.

The resulting mixture was diluted with about 35 ml. of water at room temperature and transferred to two 50 ml. centrifuge tubes. The tubes' contents were centrifuged and the supernatant liquids were discarded. The residues from the tubes were combined and washed in sequence with about 40 ml. of cold 0.2% acetic acid solution, 40 ml. of cold water and 40 ml. of cold 0.2% acetic acid solution. This last wash was to remove the last traces of furoic acid byproduct of the hydrolysis reaction. This byproduct can be eliminated in future batches with more thorough first washes. The wash liquids were centrifuged and the supernatant liquids were discarded. The resulting suspension of the above-named disulfide end product showed an 83.6% purity of the end product compound.

The residue was suspended in about 20 ml. of water and transferred to a 250 ml. round-bottomed flask and the mixture was lyophilized to obtain a yield of 0.35 gm. of the titled disulfide (85% of theory), having a purity of 85.75% by HPLC analysis procedures.

The titled disulfide product of this detailed example can also be named as 5-thia-1-azabicyclo(4.2.0)oct-2-ene-2-carboxylic acid, 3,3'-[dithiobis(methylene)]-bis[7-[[(2-amino-1,3-thiazol-4-yl)(methoxyimino)-)acetyl]amino]-8-[6R-[3[6'R,7'S-Z0],6α-7β-(Z)]]- by the Chemical Abstracts nomenclature system.

EXAMPLE 6

This example illustrates the effectiveness of the Formula V compound of this invention as an antibiotic against a variety of gram-negative veterinary pathogenic microorganisms compared against ceftiofur and desacetylcefotoxime in terms of the minimum inhibitory concentration (MIC values), in standard laboratory tests conducted as follows:

Stock solutions of each test antibiotic compound were prepared to have a concentration of 2 mg. of the test compound per milliliter in sterile water of 0.1M ammonium acetate solution. The amount of each compound used was adjusted for base compound activity as calculated from the purity data for the selected batch of compound.

The dilution procedure described by Washington and Sutter [*Manual of Clinical Microbiology*, 3rd, Edit. (Lennett, E. H. et al, Eds.), pp. 453-458 (1980), American Society for Microbiology, Washington, D.C.] was modified so that serial concentrations of 128 to 0.0625 microgram/ml. in sterile water was obtained. Then 1.5 ml. aliquots of these test antibiotic dilution mixtures are added to 13.5 molten (50° C.) Mueller-Hinton agar. Each resulting mixture is poured into 15×100 mm, sterile Petri plates and allowed to dry at room temperature overnight.

Test bacterial cultures are maintained at −70° C. on glass beads. [See R. J. Yancey, Jr. et al, *Amer. Jr. of Vet. Research*, 48, No. 7, pp. 1050-1053, (1987)]. At least one bacteria-laden bead per culture is dropped into one ml. of brain heart infusion (BHI) broth for overnight culture at 37° C. in 5% V/V carbon dioxide in air atmosphere.

On the data of assay, 2 to 8 drops of the bacterial broth cultures are transferred to fresh BHI broth (1 ml.) and the mixture is incubated for 4 to 6 hours at 37° C. in a 5% V/V carbon dioxide in air atmosphere. The resulting cultures are then diluted to match a 0.5 MacFarland standard and further diluted 1:20 V/V with sterile saline solution.

A 0.001 ml. drop of the resulting mixture, containing approximately $10^3$ to $10^4$ colony forming units (CFU) of each test bacteria organism, is dispensed onto the surface of the test antibiotic compound test plates with a Steer's type replicator. The resulting innoculated plates are incubated 16 to 18 hours at 37° C. with a carbon dioxide atmosphere. The minimal inhibitory concentration (MIC) is determined as the lowest concentration of test compound antibiotic that completely inhibited visable growth of the test bacterium.

TABLE IV

MINIMAL INHIBITORY CONCENTRATION (MIC) DETERMINATIONS FOR VETERINARY PATHOGENS

| ORGANISM | STRAIN | MIC 9μ/ML) (Example 5 Compound) |
|---|---|---|
| Staphylococcus aureus | UC6093 | 16 |
|  | UC6097 | 16 |
|  | UC9203 | 16 |
| Streptococcus agalactiae | UC3947 | ≦0.06 |
|  | UC6892 | ≦0.06 |
| Streptococcus bovis | UC6281 | ≦0.06 |
| Streptococcus dysgalactiae | UC251 | ≦0.06 |
| Enterococcus faecium | UC241 | >32 |
| Enterococcus faecalis | UC694 | >32 |
| Streptococcus suis | 650-2 | ≦0.06 |
| Streptococcus uberis | UC3946 | 0.25 |
|  | UC6159 | 16 |
| Micrococcus luteus | UC130 | ≦0.06 |
| Cornebacterium pyogenes | 213-2 | 0.25 |
| Pasturella hemolytica | UC6531 | ≦0.06 |
|  | UC6532 | ≦0.06 |
|  | UC9582 | ≦0.06 |
| Pasturella multocida | UC9581 | ≦0.06 |
| Bordetella bronchiseptica | UC6313 | >32 |
| Escherichia coli | UC3784 | 2 |
|  | UC6720 | 2 |
|  | UC9670 | 2 |
| Salmonella cholaesuis | UC6073 | 4 |
|  | UC6077 | 8 |
| Salmonella typhimurium | UC6162 | 2 |
|  | UC6164 | 2 |
| Pseudomonas aeruginosa | ATCC 27853 | >32 |

EXAMPLE 7

Preparation of
7-[2-(2-amino-1,3-thiazol-4-yl)-2-(methoxyimino)acetamido]-3-(aminocarbonylmethylthiomethyl)-3-cephem-4-carboxylic acid from sodium ceftiofur A 200 mg. portion of sodium ceftiofur, [sodium 7-2-(2-amino-1,3-thiazol-4-yl)-2-(methoxyamino)acetamido]-3-[(fur-2-yl-carbonyl)thiomethyl]-3-cephem-4-carboxylate] was dissolved in 8 ml. of 0.1M sodium bicarbonate in water solution in a 15 ml. test tube. To this solution there was added 300 mg. of dithioerythritol (DTE). The top area of the test tube reaction vessel was flushed with nitrogen to remove air atmosphere. The tube reaction vessel was heated in a water bath to 45 to 50 degrees C. to ensure dissolution of the DTE, and to effect the hydrolysis reaction to remove the furoyl group from the starting cephalosporin and to form the 3-mercaptomethyl group intermediate compound. This hydrolysis reaction was complete in about 1 to 1.5 hours.

The reaction vessel tube was removed from the warm water bath and the contents thereof was treated with 1 gm. of iodoacetamide and 33 microliters of triethylamine (TEA) as a halogen absorber. The tube reaction vessel was capped with aluminum foil over a nitrogen atmosphere in the tube. Periodically, the mixture was checked for the percent of completion of the thiol group etherification. The reaction was complete within about one hour to form the 3-aminocarbonylmethylthiomethyl derivative compound. The reaction mixture was acidified with about 1 ml. of 1N hydrochloric acid or a little more to pH about 2 for purification of the mixture on a silica gel chromatography column. The column contained a 1.5 cm. by 7 cm. $C_{18}$ silica, Waters 55 to 105 micrometers conditioned by first passing 0.01N methanolic hydrochloric acid followed by 0.01N hydrochloric acid through the column. After applying the reaction mixture sample to the column, the column was eluted with 75 ml. of 0.01N hydrochloric acid. The fractions of liquid coming from the column which contained the furoic acid, excess DTE and iodoacetamide was discarded.

Then the column was eluted with 80 percent methanol in 0.01N hydrochloric acid. The first 5 ml. of effluent from the column were discarded. The next 15 ml. of effluent from the column was collected which contained all of the desired and titled end product compound.

The 15 ml. of solution containing the desired 3-(aminocarbonylmethylthiomethyl)ceftiofur derivative was transferred to a 250 ml. round bottomed flask. To the contents in the flask there was added 15 to 20 ml. of water. The resulting mixture was frozen and lyophilized to obtain the titled end product derivative compound as a white powder, having a high performance liquid chromatography (HPLC) purity of 80.09 percent. The yield was 165 mg (93 percent of theory).

EXAMPLE 8

This example illustrates the effectiveness of the Formula VII compound of this invention as an antibiotic against a variety of gram-negative veterinary pathogen microorganisms compared against ceftiofur and desacetylcefotoxime in terms of the minimum inhibitory concentration (MIC values), in standard laboratory tests conducted as follows:

Stock solution of each test antibiotic compound were prepared to have a concentration of 2 mg. of the test compound per milliliter in sterile water of 0.1M ammonium acetate solution. The amount of each compound used was adjusted for base compound activity as calculated from the purity data for the selected batch of compound.

The dilution procedure described by Washington and Sutter [*Manual of Clinical Microbiology*, 3rd, Edit. (Lennett, E. H. et al, Eds.), pp. 453–458 (1980), American Society for Microbiology, Washington, D.C.] was modified so that serial concentrations of 128 to 0.0625 microgram/ml. in sterile water was obtained. Then 1.5 ml. aliquots of these test antibiotic dilution mixtures are added to 13.5 molten (50° C.) Mueller-Hinton agar. Each resulting mixture is poured into 15×100 mm. sterile Petri plates and allowed to dry at room temperature overnight.

Test bacterial cultures are maintained at −70° C. on glass beads. [See R. J. Yancey, Jr. et al, *Amer. Jr. of Vet. Research*, 48, No. 7, pp. 1050–1053, (1987)]. At least one bacteria-laden bead per culture is dropped into one ml. of brain heart infusion (BHI) broth for overnight culture at 37° C. in 5% V/V carbon dioxide in air atmosphere.

On the data of assay, 2 to 8 drops of the bacterial broth cultures are transferred to fresh BHI broth (1 ml.) and the mixture is incubated for 4 to 6 hours at 37° C. in a 5% V/V carbon dioxide in air atmosphere. The resulting cultures are then diluted to match a 0.5 MacFarland standard and further diluted 1:20 V/V with sterile saline solution.

A 0.001 ml. drop of the resulting mixture, containing approximately $10^3$ to $10^4$ colony forming units (CFU) of each test bacteria organism, is dispensed onto the surface of the test antibiotic compound test plates with a Steer's type replicator. The resulting innoculated plates are incubated 16 to 18 hours at 37° C. with a carbon dioxide atmosphere. The minimal inhibitory concentration (MIC) is determined as the lowest concentration of test compound antibiotic that completely inhibited visable growth of the test bacterium.

By these in vitro procedures the MIC values of the Formula VII compound were determined against the organisms listed in TABLE V and are listed there.

The MIC data in TABLE V illustrates that the Formula VII compound of this invention is an effective antibiotic at the indicated MIC concentrations against most of the organisms and is particularly effective against *Escherichia coli* and Salmonella sp. Results against the *Salmonella typhimurium* are illustrative of a longer serum half life for the Formula VII compound.

Such a property in an antibiotic compound is desirable for use against infections by bacteria such as *Salmonella typhimurium* which are known to persist in tissues.

TABLE V

| Minimal Inhibitory Concentration (MIC) Determinations for Veterinary Pathogens | | |
|---|---|---|
| Organism | Strain | MIC (μg/ml) (Example 7 compound) |
| *Staphylococcus aureus* | UC6093 | 4 |
| | UC6097 | 4 |
| | UC9203 | 4 |
| *Streptococcus agalactiae* | UC3947 | ≦0.06 |
| | UC6892 | ≦0.06 |
| *Streptococcus bovis* | UC6281 | 0.13 |

TABLE V-continued

Minimal Inhibitory Concentration (MIC)
Determinations for Veterinary Pathogens

| Organism | Strain | MIC (μg/ml) (Example 7 compound) |
|---|---|---|
| *Streptococcus dysgalactiae* | UC251 | ≦0.06 |
| *Enterococcus faecium* | UC241 | >32 |
| *Enterococcus faecalis* | UC694 | >32 |
| *Streptococcus suis* | 650-2 | 0.13 |
| *Streptococcus uberis* | UC3946 | 0.13 |
| | UC6159 | 32 |
| *Micrococcus luteus* | UC130 | 0.25 |
| *Corynebacterium pyogenes* | 213-2 | 16 |
| *Pasteurella hemolytica* | UC6531 | ≦0.06 |
| | UC6532 | ≦0.06 |
| | UC9582 | ≦0.06 |
| *Pasteurella multocida* | UC9581 | ≦0.06 |
| *Bordetella bronchiseptica* | UC6313 | >32 |
| *Escherichia coli* | UC3784 | 1 |
| | UC6720 | 1 |
| | UC9670 | 1 |
| *Salmonella choleraesuis* | UC6073 | 1 |
| | UC6077 | 2 |
| *Salmonella typhimurium* | UC6162 | 1 |
| | UC6164 | 1 |
| *Pseudomonas aeruginosa* | ATCC 27853 | >32 |

EXAMPLE 9

Preparation of methyl desfuroyl ceftiofur disulfide, 7-[2-(2-amino-1,3-thiazo-4-yl]-2-(methoxyimino)acetamimdo]-3-methyldithiomethyl-3-cephem-4-carboxylic acid A 0.536 gm (1.25 mmol) portion of desfuroylceftiofur, 7-[2-(2-amino-1,3-thiazo-4-yl)-2-(methoxyimino)acetamimdo]-3-mercaptomethyl-3-cephem-4-carboxylic acid, obtained as described hereinabove, was dissolved in 10 ml. of water and the resulting solution was cooled to 0 degrees C. in an ice bath. To this cooled, stirred solution there was slowly added 0.15 ml., 0.18 gm. (1.46 mmol) of methyl methanethiol sulfonate in 2.5 ml. of ethanol. The resulting mixture was stirred at 0 degrees C. for 1.5 hours and then a sample thereof was analyzed by HPLC procedures, which analysis showed that no desfuroylceftiofur starting material was present. The resulting reaction mixture was filtered and washed with cold ethanol followed by a wash with cold water. The residue was dissolved in ethanol and then filtered to separate some unwanted insoluble material. Hexane, 10 ml., was added to the ethanol filtrate solution causing the precipitation of white solid material which was filtered. HPLC analysis of a sample of this white precipitate showed it to be mostly the above titled product, and other impurities. So ice-cold water (20 ml.) was added to the ethanol/hexane filtrate, precipitating additional white solid material which was filtered and washed with water. This latter white solid product was analyzed to be greater than 90 percent pure by HPLC analysis. After the solid was dried in a dessicator in vacuo the yield of the titled compound was 130 mg. The fast atom bombardment (FAB) analysis of a sample of this material was consistent with the correct molecular weight of the titled product.

EXAMPLE 10

Preparation of Ethyl Desfuroylceftiofur disulfide, 7-[2-(2-amino-1,3-thiazol-4-yl)-2-(methoxyimino)acetamido]-3-ethyldithiomethyl-3-cephem-4-carboxylic acid, from sodium ceftiofur A 3.0 gm. (5.5 millimole) portion of sodium ceftiofur was dissolved in 60 ml. of water and the mixture was cooled to 0 degrees C. in an ice bath. A mixture of 1.2 gm. (7.8 millimoles) of dithioerythritol in 30 ml. of water and 1.2 ml. (8.555 millimoles) of triethylamine was added resulting in the formation of a cloudy suspension. The mixture was stirred at 0 degrees C. under nitrogen overnight. Then 3.0 gm. (0.016 mol) of iodoacetamide was added to the mixture at room temperature, and the mixture was stirred at room temperature under nitrogen for 2 hours. The pH of the mixture was adjusted to 9 by the addition of 1N sodium hydroxide and then 1.0 gm. (0.005 mol) of additional iodoacetamide was added to the mixture and the mixture was stirred at room temperature under nitrogen for five hours. The mixture was acidified to pH 3 with orthophosphoric acid resulting in the precipitation of dark viscous material which was filtered. The filtrate was concentrated in vacuo on a rotary evaporator to give a clear viscous oil with some solid. Ethanol (10 ml.) was added to the residue and since not all of the residue dissolved in ethanol, the ethanol solution was decanted into another flask, and 20 ml. of ethyl acetate was added to the solution causing the precipitation of white crystals which were filtered and washed with ethyl acetate. The additional crystals in the mother liquor were collected and washed with ethyl acetate. After drying in vacuo in a dessicator the total yield of the titled ethyl dithio- compound was 1.04 gm. This product was found to be greater than 95 percent pure by HPLC analysis. The fast atom bombardment (FAB) mass spectrum for a sample of this material was consistent with the corrected molecular weight of the titled product.

EXAMPLES 11 TO 19

General procedure for preparing 3-(R-S-S-methyl)-7β-[2-(2-amino-1,3-thiazol-4-yl)-(Z)-2-(methoxyimino)acetamido]ceph-3-em-4-carboxylic acid compounds where R- is n-propyl, n-butyl, sec-butyl, phenyl, 4-chlorophenyl, 4-nitrophenyl, benzyl, furfur-2-yl or cyclohexyl A mixture of 1.17 mmol of the respective N-(R-thio)phthalimide (or N-(phenylthiosuccinimide) and 1.17 mmol of desfuroylceftiofur [3-mercaptomethyl-7β-[2-amono-1,3-thiazol-4-yl)-(Z)-2-(methoxyimino)acetamido]ceph-3-em-4-carboxylic acid ] and 95 percent ethanol (10 ml.) was stirred at room temperature under nitrogen for 4 hours. The reaction mixture was filtered and washed with ethanol. Hexane (10 ml.) was added to the ethanol filtrate to precipitate a white solid. After filtering the solid, cold water (25 ml.) was added to the ethanol-hexane filtrate which precipitated a white solid material. This material was filtered, washed with water and dried to yield the desired respective products. The weight yields were no more than 240 mg.

EXAMPLE 20

This example illustrates the effectiveness of the Formula IX compounds of this invention as antibiotics against a variety of gram-negative veterinary pathogen microorganisms in terms of the minimum inhibitory concentration (MIC values), in standard laboratory tests conducted as follows:

Stock solutions of each test antibiotic compound were prepared to have a concentration of 2 mg. of the test compound per milliliter in sterile water of 0.1M ammonium acetate solution. The amount of each compound used was adjusted for base compound activity as calculated from the purity data for the selected batch of compound.

The dilution procedure described by Washington and Sutter [*Manual of Clinical Microbiology*, 3rd, Edit. (Lennett, E. H. et al, Eds.), pp. 453–458 (1980), American Society for Microbiology. Washington, D.C.] was modified so that serial concentrations of 128 to 0.0625 microgram/ml. in sterile water was obtained. Then 1.5 ml. aliquots of these test antibiotic dilution mixtures are added to 13.5 molten (50° C.) Mueller-Hinton agar. Each resulting mixture is poured into 15×100 mm. sterile Petri plates and allowed to dry at room temperature overnight.

Test bacterial culture are maintained at −70° C. on glass beads. [See R. J. Yancey, Jr. et al, *Amer. Jr. of Vet. Research*, 48, No. 7, pp. 1050–1053, (1987)]. At least one bacteria-laden bead per culture is dropped into one ml. of brain heart infusion (BHI) broth for overnight culture at 37° C. in 5% V/V carbon dioxide in air atmosphere.

On the day of assay, 2 to 8 drops of the bacterial broth cultures are transferred to fresh BHI broth (1 ml.) and the mixture is incubated for 4 to 6 hours at 37° C. in a 5% V/V carbon dioxide in air atmosphere. The resulting cultures are then diluted to match a 0.5 MacFarland standard and further diluted 1:20 V/V with sterile saline solution.

A 0.001 ml. drop of the resulting mixture, containing approximately $10^3$ to $10^4$ colony forming units (CFU) of each test bacteria organism, is dispensed onto the surface of the test antibiotic compound test plates with a Steer's type replicator. The resulting innoculated plates are incubated 16 to 18 hours at 37° C. with a carbon dioxide atmosphere. The minimal inhibitory concentration (MIC) is determined as the lowest concentration of test compound antibiotic that completely inhibited visable growth of the test bacterium.

By these in vitro procedures the MIC values of the Formula IX compounds were determined against the organisms listed in the Tables below.

The MIC data listed in the Tables below illustrate that the Formula IX compounds of this invention are effective antibiotics at comparative MIC concentrations against most of the organisms. Results against the *Salmonella typhimurium* are illustrative of a longer serum half life for the Formula IX compound due to its interaction via its mercapto (or sulfhydroyl) moiety with serum and tissue proteins.

Such a property in an antibiotic compound is desirable for use against infections by bacteria such as *Salmonella typhimurium* which are known to persist in tissues.

The 3-(methyldithiomethyl) and 3-(ethyldithiomethyl) compounds of Examples 9 and 10 exhibited the following Minimum Inhibitory Concentration (MIC) values in standard in vitro tests against the following veterinary pathogen organisms.

TABLE VI

| Organism | Strain | MIC (µg/ml) Example, R =) | |
|---|---|---|---|
| | | 9 methyl | 10 ethyl |
| Staphylococcus aureus | UC6093 | 2 | 4 |
| | UC6097<sup>a</sup> | 2 | 2 |
| | UC9203<sup>a</sup> | 2 | 2 |
| Streptococcus agalactiae | UC3947 | ≦0.06 | 2 |
| | UC6892 | ≦0.06 | >32 |
| Streptococcus bovis | UC6281 | ≦0.06 | >32 |
| Streptococcus dysgalactiae | UC251 | ≦0.06 | ≦0.06 |
| Enterococcus faecium | UC241 | >32 | 32 |
| Enterococcus faecalis | UC694 | >32 | 32 |
| Streptococcus suis | 650-2 | ≦0.06 | ≦0.06 |
| Streptococcus uberis | UC3946 | 0.13 | 0.25 |
| | UC6159 | 16 | >32 |
| Micrococcus luteus | UC130 | 0.13 | 0.5 |
| Corynebacterium pyogenes | 213-2 | 0.5 | 32 |
| Pasteurella hemolytica | UC6531 | ≦0.06 | 0.25 |
| | UC6532<sup>a</sup> | ≦0.06 | 0.25 |
| | UC9582<sup>a</sup> | ≦0.06 | 0.5 |
| Pasteurella multocida | UC9581 | ≦0.06 | 4 |
| Bordetella bronchiseptica | UC6313 | >32 | 16 |
| Escherichia coli | UC3784 | 1 | 4 |
| | UC6720<sup>a</sup> | 1 | 8 |
| | UC9670 | 1 | 4 |
| Salmonella choleraesuis | UC6073 | 1 | 16 |
| | UC6077 | 4 | 32 |
| Salmonella typhimurium | UC6162 | 1 | 8 |
| | UC6164<sup>a</sup> | 1 | 8 |
| Pseudomonas aeruginosa | ATCC 27853 | >32 | >32 |

The 3-(propyldithiomethyl)-, 3-(n-butyldithiomethyl)-, 3-(sec-butyldithiomethyl)- compounds, Examples 11, 12 and 13, respectively, gave the following antibiotic MIC numbers against the indicated veterinary pathogen organisms in standard laboratory tests.

TABLE VII

| Organism | Strain | MIC (µg/ml) Example, R-) | | |
|---|---|---|---|---|
| | | 11 n-propyl | 12 n-butyl | 13 sec-butyl |
| Staphylococcus aureus | UC6093 | 8 | 4 | 4 |
| | UC6097<sup>a</sup> | 8 | 4 | 2 |
| | UC9203<sup>a</sup> | 8 | 4 | 2 |
| Streptococcus agalactiae | UC3947 | 2 | 2 | 2 |
| | UC6892 | >32 | >32 | >32 |
| Streptococcus bovis | UC6281 | >32 | >32 | >32 |
| Streptococcus dysgalactiae | UC251 | ≦0.06 | ≦0.06 | ≦0.06 |
| Enterococcus faecium | UC241 | >32 | >32 | >32 |
| Enterococcus faecalis | UC694 | >32 | >32 | >32 |
| Streptococcus suis | 650-2 | ≦0.06 | ≦0.06 | ≦0.06 |
| Streptococcus uberis | UC3946 | 0.25 | 0.13 | 0.13 |
| | UC6159 | 16 | 8 | 8 |
| Micrococcus luteus | UC130 | 0.5 | ≦0.06 | 0.13 |
| Corynebacterium pyogenes | 213-2 | >32 | 32 | 32 |
| Pasteurella hemolytica | UC6531 | 0.5 | 0.5 | 1 |
| | UC6532<sup>a</sup> | 0.5 | 0.5 | 0.13 |

TABLE VII-continued

| | | MIC (µg/ml) Example. R- ) | | |
|---|---|---|---|---|
| Organism | Strain | 11 n-propyl | 12 n-butyl | 13 sec-butyl |
| | UC9582ª | 0.5 | 0.5 | 0.25 |
| Pasteurella multocida | UC9581 | 32 | 8 | 8 |
| Bordetella bronchiseptica | UC6313 | 32 | >32 | >32 |
| Escherichia coli | UC3784 | 16 | 8 | 8 |
| | UC6720ª | 32 | 16 | 16 |
| | UC9670 | 16 | 8 | 8 |
| Salmonella choleraesuis | UC6073 | 32 | 32 | 32 |
| | UC6077 | >32 | 32 | >32 |
| Salmonella typhimurium | UC6162 | 16 | 16 | 16 |
| | UC6164ª | 32 | 32 | 16 |
| Pseudomonas aeruginosa | ATCC 27853 | >32 | >32 | >32 |

The 3-(benzyldithiomethyl)-, 3-(phenyldithiomethyl)- and 3-(2-furfuryldithiomethyl)- compounds, Examples 14, 15 and 16 respectively, gave the following antibiotic MIC numbers against the indicated veterinary pathogen organisms in standard laboratory tests.

The 3-(4-chlorophenyldithiomethyl)-, 3-(4nitrophenyldithiomethyl) and 3-(cyclohexyldithiomethyl)- compounds, Examples 17, 18 and 19, respectively, gave the following antibiotic MIC numbers against the indicated veterinary pathogen organisms in standard labo-

TABLE VIII

| | | MIC (µg/ml) Example. R- ) | | |
|---|---|---|---|---|
| Organism | Strain | 14 benzyl | 15 phenyl | 16 furfuryl |
| Staphylococcus aureus | UC6093 | 1 | 2 | 1 |
| | UC6097ª | 1 | 2 | 2 |
| | UC9203ª | 1 | 2 | 1 |
| Streptococcus agalactiae | UC3947 | NGᶜ | ≦0.06 | ≦0.06 |
| | UC6892 | ≦0.06 | ≦0.06 | ≦0.06 |
| Streptococcus bovis | UC6281 | ≦0.06 | ≦0.06 | ≦0.06 |
| Streptococcus dysgalactiae | UC251 | ≦0.06 | ≦0.06 | ≦0.06 |
| Enterococcus faecium | UC241 | >32 | >32 | >32 |
| Enterococcus faecalis | UC694 | >32 | >32 | >32 |
| Streptococcus suis | 650-2 | ≦0.06 | ≦0.06 | ≦0.06 |
| Streptococcus uberis | UC3946 | ≦0.06 | ≦0.06 | ≦0.06 |
| | UC6159 | 8 | 16 | 4 |
| Micrococcus luteus | UC130 | ≦0.06 | ≦0.06 | ≦0.06 |
| Corynebacterium pyogenes | 213-2 | 0.25 | 4 | 0.13 |
| Pasteurella hemolytica | UC6531 | 0.5 | 0.13 | 0.25 |
| | UC6532ª | 0.25 | 0.25 | 0.13 |
| | UC9582ª | 2 | 0.25 | 0.13 |
| Pasteurella multocida | UC9581 | 2 | ≦0.06 | 1.0 |
| Bordetella bronchiseptica | UC6313 | >32 | >32 | >32 |
| Escherichia coli | UC3784 | 8 | 8 | 4 |
| | UC6720ª | 16 | 8 | 8 |
| | UC9670 | 8 | 8 | 4 |
| Salmonella choleraesuis | UC6073 | 16 | 32 | 16 |
| | UC6077 | 32 | 32 | 32 |
| Salmonella typhimurium | UC6162 | 16 | 16 | 16 |
| | UC6164ª | 16 | 8 | 8 |
| Pseudomonas aeruginosa | ATCC 27853 | >32 | >32 | >32 | ratory tests.

TABLE IX

| | | MIC (µg/ml) Example, R- ) | | |
|---|---|---|---|---|
| Organism | Strain | 17 4-Cl-O | 18 4-NO₂-O | 19 cyclohexyl |
| Staphylococcus aureus | UC6093 | 4 | 2 | 1 |
| | UC6097ª | 2 | 2 | 1 |
| | UC9203ª | 2 | 2 | 1 |
| Streptococcus agalactiae | UC3947 | ≦0.06 | ≦0.06 | ≦0.06 |
| | UC6892 | ≦0.06 | ≦0.06 | ≦0.06 |
| Streptococcus bovis | UC6281 | ≦0.06 | ≦0.06 | ≦0.06 |
| Streptococcus dysgalactiae | UC251 | ≦0.06 | ≦0.06 | ≦0.06 |
| Enterococcus faecium | UC241 | >32 | >32 | >32 |
| Enterococcus faecalis | UC694 | >32 | >32 | >32 |
| Streptococcus suis | 650-2 | ≦0.06 | ≦0.06 | ≦0.06 |
| Streptococcus uberis | UC3946 | ≦0.06 | 0.25 | 0.13 |
| | UC6159 | 4 | 8 | 8 |
| Micrococcus luteus | UC130 | ≦0.06 | ≦0.06 | ≦0.06 |
| Corynebacterium pyogenes | 213-2 | ≦0.06 | 0.25 | 0.5 |
| Pasteurella hemolytica | UC6531 | ≦0.06 | 0.25 | 0.5 |

TABLE IX-continued

| | | MIC (μg/ml) Example, R- ) | | |
|---|---|---|---|---|
| Organism | Strain | 17 4-Cl-O | 18 4-NO₂-O | 19 cyclohexyl |
| | UC6532ᵃ | 0.13 | ≦0.06 | 0.5 |
| | UC9582ᵃ | 0.13 | ≦0.06 | 0.25 |
| Pasteurella multocida | UC9581 | ≦0.06 | ≦0.06 | ≦0.06 |
| Bordetella bronchiseptica | UC6313 | >32 | >32 | >32 |
| Escherichia coli | UC3784 | 2 | 1 | 4 |
| | UC6720ᵃ | 4 | 2 | 8 |
| | UC9670 | 8 | 1 | 4 |
| Salmonella choleraesuis | UC6073 | 8 | 2 | 8 |
| | UC6077 | 8 | 4 | 16 |
| Salmonella typhimurium | UC6162 | 4 | 4 | 16 |
| | UC6164ᵃ | 4 | 2 | 16 |
| Pseudomonas aeruginosa | ATCC 27853 | >32 | >32 | >32 |

EXAMPLE 21   Oral Suspension

One thousand cc. of an aqueous suspension for oral use, containing in each 1 ml. dose 5 to 300 mg. of any Formula I compound is prepared from the following types of and amounts of ingredients.

| | |
|---|---|
| Formula I compound (powder) | 5 to 300 gms. |
| Benzoic Acid or Sorbic Acid | 1 gm. |
| Sucrose | 650 gms. |
| Sodium Carboxymethylcellulose, Low Viscosity | 1 to 20 gms. |
| Flavors (e.g. USP cherry, orange) | q.s. |
| Sodium Chloride (0.5 to 10 mg./ml.) | 0.5 to 10 gms. |
| Hydrochloric Acid, Reagent Grade | q.s. adjust pH to approximately 3.0 |
| Deionized Water | q.s. to 1000 cc. |

The sodium carboxymethylcellulose, benzoic acid, sucrose, appropriate flavors and sodium chloride are dispersed in sufficient water to make 650 mls. of solution. The Formula I compound is stirred into the syrup until uniformly distributed. The resulting suspension is colloid milled to a uniform consistency. Sufficient water is added to bring volume to 900 cc. If necessary pH is adjusted with hydrochloric acid to about pH3. Sufficient water is added to make 1000 cc.

EXAMPLE 22   Sterile Parenteral Suspension

Sterile Vehicle—Part I

| | |
|---|---|
| PEG | 5 to 120 gms. |
| Benzyl Alcohol, or | 9.1 gm. |
| Benzoic Acid | 1.0 gm. |
| Povidone | 1 to 10 gms. |
| Sodium Chloride Fine Crystals, Reagent Grade | 9 gms. |
| Hydrochloric Acid, Reagent Grade | q.s. adjust pH to approximately 3.0 |
| 50% Solution Sodium Hydroxide | q.s. adjust pH 3.0 |
| Water for Injection | q.s. adjust 1000 cc. |

Part II

| | |
|---|---|
| Formula I compound, powder | 1.0 to 100 gms. |
| Vehicle Part I | q.s. adjust 1000 cc. |

DIRECTIONS

Part I

All of the ingredients are dissolved in water and pH adjusted to about 2.6 to 3.2, preferably about 3.0. The vehicle is sterilized by filtration and used in Part II.

Part II

Aseptically add sterile Formula I compound in sufficient vehicle from Part I to make 900 mls. Stir the suspension and colloid mill the suspension to a uniform consistency. Add sufficient vehicle to make 1000 mls.

EXAMPLE 23   Sterile Parenteral Suspension

Sterile Vehicle—Part I

| | |
|---|---|
| Polysorbate 80, N.F. | 0.1 to 10 gms. |
| Sodium Carboxymethylcellulose, low viscosity | 2 to 20 gms. |
| Benzyl Alcohol | 9.1 gms. |
| Benzoic Acid | 0.2 to 2.0 gms. |
| Povidone | 1 to 10 gms. |
| Sodium Chloride, Fine Crystals Reagent | if needed 9 gms. |
| Hydrochloric Acid, Reagent Grade | q.s. adjust pH to approximately 3.0 |
| 50% Solution Sodium Hydroxide | q.s. adjust pH 3.0 |
| Water for Injection | q.s. adjust 1000 cc. |

Part II

| | |
|---|---|
| Formula I compound, powder | 1.0 to 100 gms. |
| Vehicle Part I | q.s. adjust 1000 cc. |

DIRECTIONS

Part I

All of the ingredients are dissolved in water and the vehicle sterilized by filtration.

Part II

Aseptically add sterile Formula I compound in sufficient vehicle to make 900 mls. Stir the suspension and pass through colloid mill to a uniform consistency. Add sufficient vehicle to make 1000 mls.

EXAMPLE 24   Sterile Parenteral Suspension

Sterile Vehicle—Part I

| | |
|---|---|
| PEG 3350 NF | 5 to 120 gms. |
| Benzyl Alcohol | 9.1 gms. |
| Benzoic Acid | 0.2 to 2.0 gms. |
| Polysorbate 80 NF Food Grade | 1 to 5 gms. |
| Sodium Chloride Fine Crystals Reagent | 0.5 to 10 gms. |
| Hydrochloric Acid, Reagent Grade | q.s. adjust pH to approximately 3.0 |
| 50% Solution Sodium Hydroxide | q.s. adjust pH 3.0 |

-continued

| | |
|---|---|
| Water for Injection | q.s. adjust 1000 cc. |

Part II

| | |
|---|---|
| Formula I compound, powder | 1 to 100 gms. |
| Vehicle Part I | q.s. adjust 1000 cc. |

DIRECTIONS

Part I

All of the ingredients are dissolved in water and pH adjusted to approximately 3.0, and the vehicle sterilized by filtration.

Part II

Aseptically add sterile Formula I compound in sufficient vehicle from Part I to make 900 mls. Stir the suspension and pass through a colloid mill to a uniform consistency. Add sufficient vehicle to make 1000 mls.

EXAMPLE 25   Sterile Extemporaneous Parenteral Suspension (Aqueous)

Sterile Vehicle—Part I

| | |
|---|---|
| Benzyl Alcohol or | 9.1 gms. or |
| Benzoic Acid | 0.2 to 2.0 gms. |
| Carboxymethylcellulose Sodium USP low viscosity or any other viscosity inducing agent | 1.0 to 20.0 gms. |
| Sodium Chloride Fine Crystals, Reagent Grade | 0.5 to 10 gms. |
| Hydrochloric Acid, Reagent Grade | q.s. adjust pH to approximately 3.0 |
| Water for Injection | |

Part II   Amount per Vial

| | |
|---|---|
| Sterile Formula I compound in a 10 to 100 ml. glass vial | 0.01 to 1.5 gm. |

DIRECTIONS

Part I

All of the ingredients are dissolved in water, and pH adjusted to approximately 2.6 to 3.2, preferably about 3.0. Vehicle sterilized by filtration and packaged in appropriate glass vials.

Part II

A sterile powdered Formula I compound is packaged aseptically in sterile vials or a crystalline Formula II compound is first packaged and the final container(s) sterilized by Cobalt 60 irradiation.

EXAMPLE 26   Sterile Extemporaneous Parenteral Suspension

Sterile Vehicle Part I

| | |
|---|---|
| Methylparaben | 1.0 to 2.7 gms. |
| Propylparaben | 0.1 to 0.5 gm. |
| Povidone | 1 to 10 gms. |
| Sodium Chloride Fine Crystals Reagent Grade | 0.5 to 10 gms. |
| 20% Solution Hydrochloric acid | q.s. adjust pH to approximately 3.0 |
| 50% Solution Sodium Hydroxide | q.s. adjust pH 3.0 |

-continued

| | |
|---|---|
| Water for Injection | q.s. adjust 1000 ccs. |

Part II   Amount Per Vial

| | |
|---|---|
| Sterile crystalline Formula II compound in a 10 to 100 ml. glass vial | 0.01 to 1.5 gm. |

DIRECTIONS

Part I

Methylparaben and propylparaben are dissolved in boiling water. Then all of the ingredients dissolved in water, and pH adjusted to approximately 2.6 to 3.2, preferably about 3.0. Vehicle sterilized by filtration and packaged in appropriate glass vials.

Part II

Sterile crystalline Formula II compound is packaged aseptically in sterile vials or crystalline Formula II compound is first packaged and the final container(s) shall be sterilized by Cobalt 60 irradiation.

EXAMPLE 27   Extemporaneous Parenteral Suspension (Aqueous)

Sterile Vehicle—Part I

| | |
|---|---|
| Polyethylene Glycol 3350 NF | 5 to 120 gms. |
| Polyvinyl Pyrrolidone | 1 to 10 gms. |
| Quatresin ® myristyl gamma picolinium chloride | 0.1 to 2.0 gms. |
| Sodium Chloride, Fine Crystals Reagent Grade | 0.5 to 10 gms. |
| 20% Solution Hydrochloric Acid | q.s. adjust pH to approximately 3.0 |
| 50% Solution Sodium Hydroxide | q.s. adjust pH to approximately 3.0 |
| Water for Injection. | q.s. adjust to 1000 cc. |

Part II   Amount Per Vial

| | |
|---|---|
| Sterile powdered Formula I compound (or an equivalent amount of a crystalline salt) (milled or micronized) in a 10 to 100 ml. glass vial | 0.01 to 1.5 gms. |

DIRECTIONS

Part I

All of the vehicle ingredients are dissolved in water, and pH adjusted to approximately 2.6 to 3.2, preferably about 3.0. Vehicle sterilized by filtration and packaged in appropriate glass vials.

Part II

Sterile powdered Formula I compound or sterile crystalline Formula II salt compound is packaged aseptically in sterile vials or first packaged and the then respective final container(s) are sterilized by Cobalt 60 irradiation.

Thereafter, just prior to use, the vehicle and drug components are mixed and then administered to the animal.

EXAMPLE 28   Sterile Nonaqueous Parenteral Suspension

| | |
|---|---|
| Powdered Formula I compound (milled | 1 to 100 gms. |

| | |
|---|---|
| or micronized) | |
| Chlorobutanol Anhydrous - preservative | 5.25 gms. |
| or | |
| Benzyl Alcohol | 9.25 gms. |
| Corn Oil Glyceryl Monostearate Gel | |
| or | |
| Cottonseed Oil Glyceryl Monostearate Gel | q.s. adjust |

DIRECTIONS

Preservative is dissolved in sufficient oily gel to make 800 cc. Powdered Formula I compound is added, and the suspension is colloid milled to a uniform consistency. Add sufficient gel to make 1000 mls. After packaging into glass vials, the suspension is sterilized by Cobalt 60 irradiation or by any other suitable method.

EXAMPLE 29   Sterile Nonaqueous Parenteral Suspension

| | |
|---|---|
| Powdered Formula I compound (milled or micronized) | 1 to 100 gms. |
| Chlorobutanol Anhydrous | 5.25 gms. |
| or | |
| Benzyl Alcohol | 9.25 gms. |
| Corn Oil USP | q.s. adjust 1000 cc. |
| or | |
| Cottonseed Oil | q.s. adjust 1000 cc. |

DIRECTIONS

Preservative is dissolved in sufficient oil to make 800 cc. Powdered Formula I compound is added, and the suspension is colloid milled to a uniform consistency to break the aggregates. Add sufficient amount of oil to make 1000 mls. Stir and package into glass vials. The suspension can be sterilized by Cobalt 60 irradiation or sterile powdered Formula I compound can be added to sterile vehicle and manufactured following aseptic procedure(s).

EXAMPLE 30—Sterile Extemporaneous Parenteral Suspension (Non-aqueous Gel)—Controlled Release Formulation Sterile Vehicle Part I   1000

| | |
|---|---|
| Benzyl Alcohol - preservative | 9.0 to 9.25 gms. |
| or | |
| Chlorobutanol | 5.0 to 5.25 gms. |
| Corn Oil Glyceryl Monostearate Gel | 1000 cc. |
| or | |
| Cottonseed Oil Glyceryl Monostearate Gel | 1000 cc. |

Part II   100 Vials

| | |
|---|---|
| Powdered Formula I compound (milled or micronized) | 1 to 100 gms. |

DIRECTIONS

Part I
Preservative is dissolved in sufficient gel, and the gel is filled into vials asceptically and the vials sealed. These vials will be packaged with the vials of Part II as companion package.
Part II
0.01 to 1.0 gm. of powdered Formula I compound or sterilized powdered Formula I compound is packaged in a sterile glass vial and the vials sealed. If the powdered Formula I compound is non-sterile, then the packaged vials will be sterilized by Cobalt 60 irradiation.

Prior to dosing appropriate amounts of Part I diluent will be added to Part II sterile powder and shaken until homogeneous.

EXAMPLE 31   Sterile Extemporaneous Parenteral Suspension (Non-aqueous)

Sterile Vehicle Part I   1000

| | |
|---|---|
| Benzyl Alcohol - preservative | 9.0 to 9.25 gms. |
| or | |
| Chlorobutanol | 5.0 to 5.25 gms. |
| Corn Oil, USP | q.s. adjust 1000 cc. |
| or | |
| Cottonseed Oil, USP | q.s. adjust 1000 cc. |

Part II   100 Vials

| | |
|---|---|
| Formula II compound, (milled and micronized) | 50 to 100 gms. |

Part I
Preservative is dissolved in the oil, and the solution sterilized by filtration. The sterile solution is filled into vials and the vials sealed. These vials will be packaged with the vials of Part II as companion package.
Part II
0.5 to 1.0 gm. of Formula I compound or sterilized Formula II compound is packaged in a sterile glass vial and the vials sealed. If the crystalline Formula II is non-sterile, then the packaged vials will be sterilized by Cobalt 60 irradiation.

Prior to dosing appropriate amounts of Part I diluent will be added to Part II sterile Formula II and shaken until uniformly mixed.

EXAMPLE 32   Suppositories

Formulation for a 2 gm. suppository containing 62.5 mg. of powdered Formula I compound is given. However, any size suppository can be manufactured using any amount of Formula I compound and appropriate amounts of excipients at the same ratio as indicated below.

| | |
|---|---|
| Lot Size 12 | |
| Formula I compound (milled or micronized) | 7.5 gm. |
| PEG-400 | 144 ml. |
| PEG-8000 | 96 gm. |

DIRECTIONS

Measure out 144 ml. of PEG-400 and place in a container suitable for heating. Add 96 gms. of PEG-8000 (melting point 140° F.) to the PEG-400 solution and melt over a hot water bath approximately two minutes or until there is a clear solution.

Add the 7.5 g. of Formula I compound and stir until dispersed. Pour the mix into the mold and let set. Chill the mold. Remove suppositories after they set up 15–30 minutes at room temperature. Sterile suppositories can be manufactured with sterile raw materials and observing aseptic conditions during manufacturing, or can be sterilized by Cobalt 60 irradiation.

EXAMPLE 33  Suppositories

Suppositories can also be manufactured from excipients such as cocoa butter, Suppocire ™ AM, Suppocire ™ AS₂, and Suppocire ™ AT, Suppocire BT or Suppocire CT brand of $C_8$ to $C_{10}$-saturated fatty acid glycerides.

Formula for a 2 gm. suppository containing 62.5 mg. of crystalline Formula II compound is given; however, any size suppository can be manufactured using any desired amount of powdered Formula I or II compound and appropriate amount of excipient.

| Lot Size 12 | |
|---|---|
| Formula II compound (milled or micronized) Sterile | 0.750 gm. |
| Suppocire AM or AS₂, or AT, or BT or CT | 23.25 gm. |

DIRECTIONS

Weight the Suppocire ™ diluent in a container suitable for heating. Melt (45° C. temperature) over a hot water bath for approximately two minutes or until there is a clear solution (microwave oven can also be used instead of the water bath. Sterilize by filtration. Add sterile Formula II compound and stir until dispersed. Pour the mix into the cold mold. After two to four minutes, the surplus of the casting is eliminated by scraping. The temperature and time of cooling must be governed according to the type of formula. The circulating cold air should come in contact with all faces of the mold. Release from the mold must be gentle. Sterile suppositories can be manufactured with sterile raw materials and observing aseptic conditions during manufacturing, or can be sterilized by Cobalt 60 irradiation.

EXAMPLE 34  Capsules

One thousand two-piece hard gelatin capsules for oral use, each containing 50 mgs. of activity of the Formula I of II compound, are prepared from the following types and amounts of materials:

| 1000 | |
|---|---|
| Formula I or II compound or Coated with Carnauba Wax ® or White Wax | (50 gms. equivalent of Formula I) |
| Talc and/or | 75 gms. |
| Magnesium Stearate | 25 gms |

Wax coated powdered Formula I or II compound will have controlled release properties. The materials are thoroughly mixed and then encapsulated in the usual manner. Different strength capsules can be prepared by changing the amounts of powdered Formula I compound.

EXAMPLE 35  Tablets

One thousand compressed tablets for oral use, each containing an amount equivalent to 50 mgs. Formula I or II compound can be prepared using the following:

| Formula I or II compound | 50 gms. |
|---|---|
| Lactose | 375 gms. |
| Corn Starch | 65 gms. |
| Magnesium Stearate | 10 gms. |

The ingredients are thoroughly mixed and slugged. The slugs are broken down by forcing through a screen. The resulting mixture is then compressed into tablets. Different strength tablets can be prepared by appropriate changes in the amounts of Formula I or II compound and the excipients.

STRUCTURES

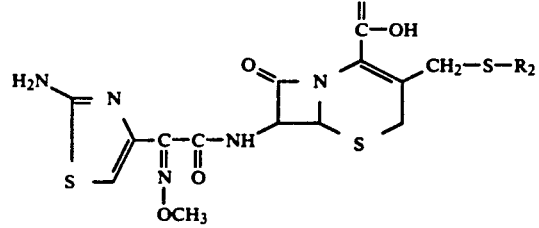

Formula I

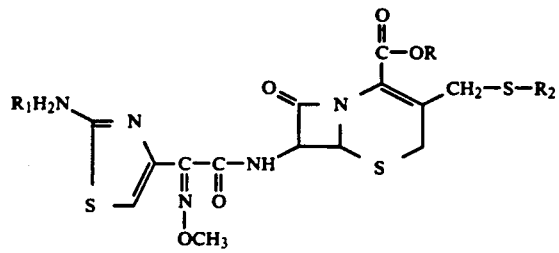

Formula II

STRUCTURES
-continued
Formula III
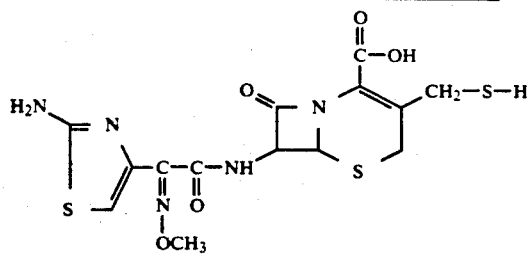
Formula IV
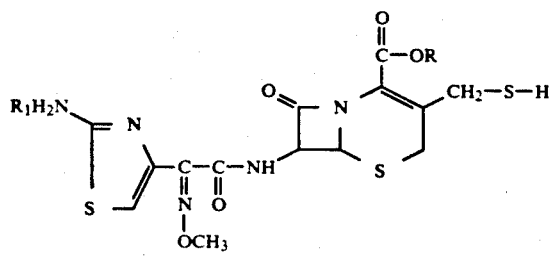
Formula V
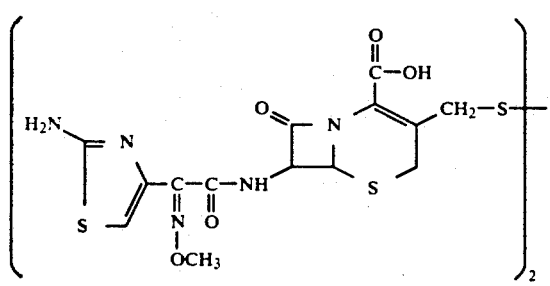
Formula VI
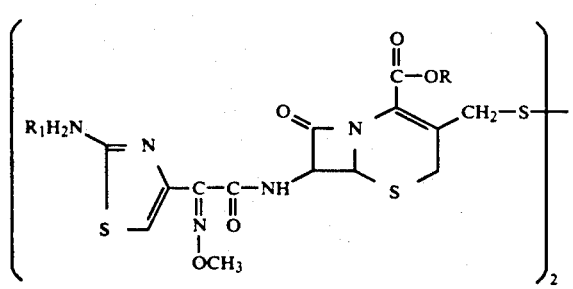
Formula VII
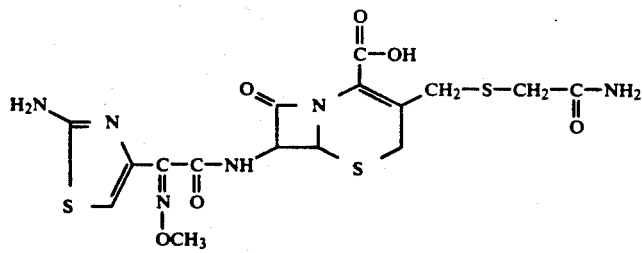
Formula VIII
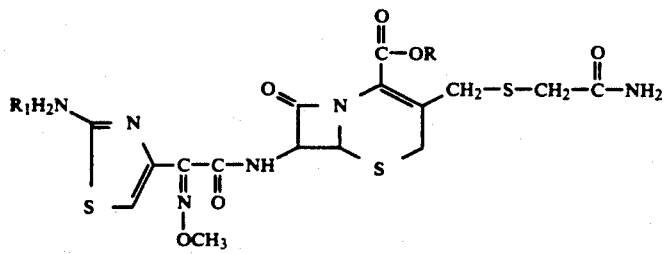

-continued

STRUCTURES

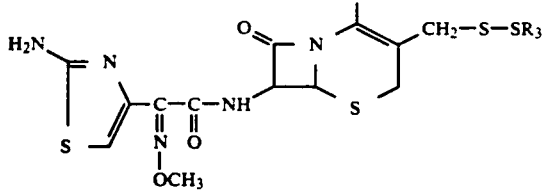

Formula IX

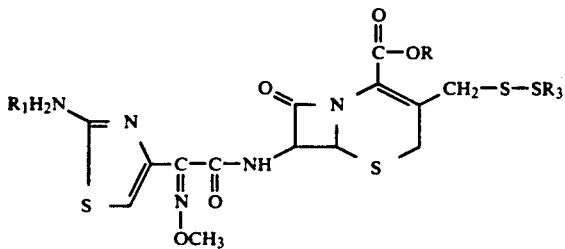

Formula X

We claim:
1. A compound of the formula

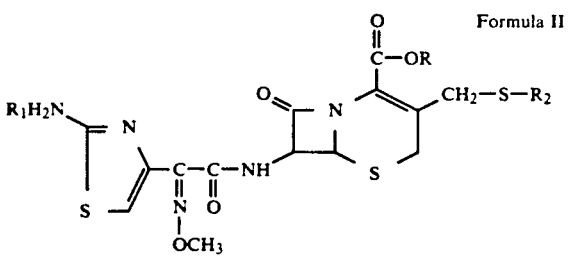

Formula II

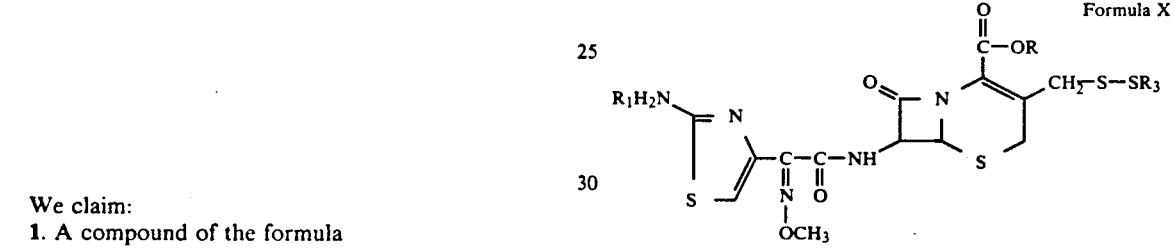

Formula X where
R is selected from the group consisting of hydrogen, a selected pharmaceutical cation or a chemical bond, when R and $R_1$ form an inner salt;
$R_1$ is an acid addition salt where R is hydrogen, or R and $R_1$ form an inner salt (Zwitterion salt), and
$R_3$ is selected from the group consisting of
$C_1$ to $C_6$-alkyl,
cyclohexyl,
phenyl,
chloro-substituted phenyl,
nitro-substituted phenyl,
benzyl, or
furfuryl,
or a pharmaceutically acceptable salt thereof.

5. A pharmaceutical composition comprising
(a) a compound of the formula II,

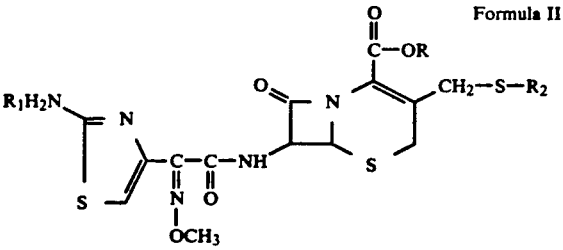

Formula II as defined in claim 1, and
(b) one or more pharmaceutically acceptable diluent carrier ingredients.

6. A method for treating a warm-blooded animal to resist, ward-off or combat Bacterial pathogen infections in said animal using the compounds as defined in claim 1.

where
R is hydrogen or a selected pharmaceutical cation, in which latter case $R_1$ is not present, or
R is hydrogen or a chemical bond when $R_1$ is an acid addition salt anion, and
$R_2$ is selected from the group consisting of
(a) hydrogen,
(b) an aminocarbonylmethyl- group, and
(c) an —$SR_3$ group where $R_3$ is a
$C_1$ to $C_6$-alkyl,
cyclohexyl,
phenyl,
chloro-substituted phenyl,
nitro-substituted phenyl,
benzyl, or
furfuryl.

2. A compound according to claim 1 which is 3-Mercaptomethyl-7β-[2-(2-amino-1,3-thiazol-4-yl)-2-(Z)-(methyoxyimino)acetamido]ceph-3-em-4-carboxylic acid, or a pharmaceutically acceptable salt thereof.

3. A compound according to claim 1 which is 3-(Aminocarbonylmethylthiomethyl)-7β-[2-(2-amino-1,3-thiazol-4-yl)-2-(Z)-(methoxyimino)acetamido]ceph-3-em-4-carboxylic acid, or a pharmaceutically acceptable salt thereof.

4. A compound according to claim 1 of the formula

* * * * *